(12) United States Patent
Leibl et al.

(10) Patent No.: US 6,646,108 B1
(45) Date of Patent: Nov. 11, 2003

(54) PROCESS FOR ISOLATING IGG AND IGA

(75) Inventors: Heinz Leibl; Regine Tomasits; Josef Mannhalter, all of Vienna; Hermann Wolf, Weidling; Martha Eibl, Vienna, all of (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/101,430

(22) PCT Filed: Jan. 9, 1997

(86) PCT No.: PCT/EP97/00067

§ 371 (c)(1),
(2), (4) Date: Jul. 9, 1998

(87) PCT Pub. No.: WO97/25352

PCT Pub. Date: Jul. 17, 1997

(30) Foreign Application Priority Data

Jan. 12, 1996 (DE) ......................... 196 00 939

(51) Int. Cl.$^7$ ..................... A61K 39/395; C07K 1/14; C07K 16/00
(52) U.S. Cl. ................ 530/387.1; 424/130.1; 424/176.1; 424/177.1; 424/804; 530/390.1; 530/390.5; 530/415; 530/416; 530/418; 530/861
(58) Field of Search ............... 530/416, 387.1, 530/391.1, 390.1, 418, 412, 415, 389.1, 390.5, 861; 436/513, 547; 424/130.1, 530, 531, 176.1, 177.1, 804; 435/2, 236, 5

(56) References Cited

U.S. PATENT DOCUMENTS

| 4,745,183 A | 5/1988 | Engelhorn et al. ........ 530/387 |
| 5,258,177 A | 11/1993 | Uemura et al. ............ 424/85.8 |
| 5,833,984 A | * 11/1998 | Eibl et al. |

FOREIGN PATENT DOCUMENTS

| AT | 383 737 | 8/1987 |
| DE | 2404265 | 7/1975 |
| DE | 3927 112 | 10/1990 |
| DE | 44 34 538 | 4/1995 |
| EP | 0 050 061 | 4/1982 |
| EP | 0 131 740 | 1/1985 |
| EP | 0 159 311 | 10/1985 |
| EP | 0 177 836 | 4/1986 |
| EP | 0 242 544 | 10/1987 |
| EP | 0 247 998 | 12/1987 |
| EP | 0 506 651 | 9/1992 |
| EP | 0692491 | 1/1996 |
| JP | 57-59815 | 4/1982 |

OTHER PUBLICATIONS

Pauling, *General Chemistry*, Second Edition, W.H. Freeman and Company, San Francisco, pp. 621–628, 1953.*
Smith et al, *Oxford Dictionary of Biochemistry and Molecular Biology*, Oxford University Press, Oxford, p. 170, 1997.*
Pauling, *General Chemistry*, Second Edition, W.H. Freeman and Company, San Francisco, p. 135, 1953.*
Skvaril et al, Coll. Czech. Chem. Comm. 30, 2886, 1965.*
Nopper et al. Anal. Biochem. 180 (1); p. 66–71, 1989.*
Leibl, H. et al., "Isolation of Human Serum IgA Using Thiophilic Adsorption Chromatography". *Protein Expression and Purification*, vol. 6; pp. 408–410 (1995).
Langone, J.J., "Applications of Immobilized Protein A in Immunochemical Techniques". *J. Immunological Methods*, vol. 55; pp. 277–296 (1982).
Wells, M. A. et al., "Inactivation and Partition of human T–cell lymphotrophic virus type III, during fractionation of plasma". *Transfusion*, vol. 26(2); pp. 210–213 (1986).
Stevens, A. "Monoclonal Antibodies". *International Biotechnology Laboratory*, vol. 3(4); pp. 33–41 (1985).
Leibl, H. et al., "Method for the isolation of biologically active monomeric immunoglobulin A from a plasma fraction". *J. Chromatography B.*, vol. 678; pp. 173–180 (1996).
Lowry, O.H. et al., "Protein Measurement with the Folin Phenol Reagent". *J. Biol. Chem.*, vol. 193; pp. 265–275 (1951).
Mancini, G. et al., "Immunochemical Quantitation of Antigens by Single Radial Immunodiffusion". *Immunochemistry*, vol. 2; pp. 235–254 (1965).

* cited by examiner

Primary Examiner—David Saunders
(74) Attorney, Agent, or Firm—Heller Ehrman White & McAuliffe

(57) ABSTRACT

A method for the separation of IgG and IgA from an immunoglobulin-containing starting material is described, whereby the method is characterized in that (i) IgG and optionally IgA are adsorbed to a solid inorganic carrier material, (ii) IgA is isolated from the eluate, optionally after selective desorption, whereas IgG remains on the carrier material, and optionally (iii) IgG is isolated from the adsorbate. Furthermore, an IgA preparation is disclosed which demonstrates a low tendency to form aggregates.

10 Claims, 4 Drawing Sheets

PROCESS FOR ISOLATING IGG AND IGA

Figure 1:
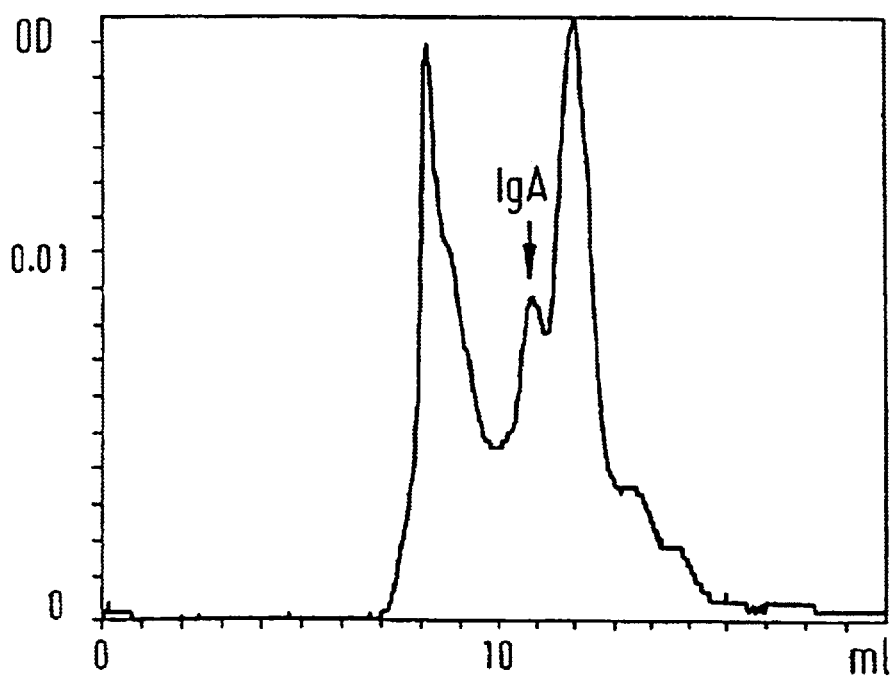

The invention relates to a process for the isolating IgG and IgA as well as the IgA solutions obtainable according to this method.

Immunoglobulins (Ig) are specific immune proteins in blood plasma, lymph and in other body secretions of all vertebrates. Immunoglobulins are synthesized from B-lymphocytes. Monomeric immunoglobulins each consist of two L (light) and H (heavy) chains which are bound to each other by disulfide bridges. Immunoglobulins are glycoproteins which function as antibodies and whose formation is stimulated by antigens. Quantitatively, they constitute approximately 20% of the total plasma proteins.

Up to now, five main classes of immunoglobulins have been identified in humans (IgA, IgD, IgE, IgG and IgM) which differ in their H-chains, in their serum concentration, molecular weight (approximately 146000 to 970000), carbohydrate content, electrophoretic mobility and their biological properties. The main classes IgA and IgG can be divided into sub-classes (for example IgA1, IgA2). The diversity of the immunoglobulin classes and subclasses as well as their diverse different specificity in binding antigens arises through combinations of various genetic building blocks.

Immunoglobulin A (IgA) represents the main antibody class in external secretions, such as saliva, tears and mucus of the bronchial and intestinal tract. Thus, immunoglobulin A forms one of the first defence lines against bacterial and viral pathogens.

In the pure monomeric form, IgA consists of two light (L) and two heavy (H) chains; in the dimeric secretory form, two such monomers are coupled by so-called J-chain (joining chain). In the secretions of the mucous membranes and glands, dimers with an additional secretory component (so-called SC-component) are present above all.

In solution, plasmatic IgA monomer is present in equilibrium with non-covalently bound IgA dimer. In this equilibrium, the maximal portion of dimeric IgA amounts to approximately 25% of the total IgA.

IgA consists of two sub-classes, IgA1 and IgA2 which are present in a native relationship of about 80% by weight to 20% by weight. This relationship can be altered in the course of isolation. The native ratio of kappa to lambda light chains (measured in U/dl) in an immunoglobulin preparation amounts to approximately 1:1.

IgA only represents approximately 3–4% of the total protein of normal human serum. During purification of IgA, a marked tendency to form complexes and aggregation has been observed. Therefore, isolation of monomeric IgA from serum was mostly associated with low yields and, up to now, only a few methods among the numerous methods of production are known which are also suitable for commercial production. Main impurities of IgA preparations are essentially the various sub-classes of immunoglobulin G whose separation requires additionally purification steps which further reduce the yield of IgA.

The known and common methods for purification of immunoglobulins are mostly based on differences in physical properties, such as for example solubility in aqueous systems (purification by fractionated precipitation), number of charges (purification by ion exchange chromatography) or a difference in the molecular size (purification by molecular size exclusion chromatography).

For a long time, inorganic carrier materials have also been used for carrying out chromatographic purification methods, for example, for the separation of plasma proteins.

Thus, Al $(OH)_3$ for example is used for separating the prothrombin complex from other proteins contained in plasma and this method is also applied on a commercial scale. Other inorganic materials, such as for example aluminium oxide, calcium phosphate or various compounds of silicon, are also preferably employed in the preparation on a commercial scale.

Hydroxylapatite which is obtained according to a special production method in sintered form is known to be employed as an adsorption agent in general chromatography from EP 242 544. Hydroxylapatite is described as a chemical substance with the formula $Ca_{10}$ $(PO_4)_6(OH)_2$, i.e. as a hydroxylated calcium phosphate, which is mostly present in particulate form. Therefore, hydroxylapatite can be considered as a particular form of calcium phosphate. Among others, Hydroxylapatite is proposed as a suitable material for the separation of biological macromolecules, for example for proteins such as immunoglobulins or enzymes or for the separation of RNA, DNA, viruses or plasmids.

A method for the production of an intravenously administerable immunoglobulin-containing pharmaceutical is known from DE 39 27 112. This pharmaceutical consists of IgA, IgG and IgM in concentrated form and is obtained by a multi-step purification process which among others also includes an absorption to calcium phosphate in the presence of caprylic acid. However, in this method, the immunoglobulins are not separated from each other, therefore, a pharmaceutical preparation is provided which contains all three groups of immunoglobulins in a certain mixed proportion.

Additionally, pharmaceutical compositions based on immunoglobulins, for example immunoglobulin A, have already been proposed for prevention and treatment of bacterial and viral infections (see JP A 478 59815).

A problem which is faced particularly using starting material of human origin for the production of immunoglobulins is the virus safety of the obtained product. Despite selection of donors and testing of the individual donor plasmas, it cannot be excluded that infectious pathogens, especially hepatitis viruses or retroviruses such as HIV are present in the pool of donations as a result of the low sensitivity of some tests for example.

Although depletion/inactivation of viruses by more than $10^{15}$ units was described in the production of an immunoglobulin preparation by fractionated alcohol precipitation according to Cohn (see Wells et al., Transfusion 26 (1986) 120–213 for example), the danger of insufficient virus inactivation, i.e. an inadequate virus safety of the preparation exists especially when using intermediate products from the Cohn fractionation.

In common methods for the inactivation of viruses, additional aggregate formation of the immunoglobulins is expected. This is demonstrated to a particular degree with methods of heat treatment which are preferably applied because, aside from lipid-coated viruses, non-lipid coated viruses (for example hepatitis A viruses) are also effectively inactivated.

It has been shown that a substantial portion of IgA can form mulitmers and/or can be polymerized during the above mentioned heat treatment. However, as explained above, aggregated IgA of this type reduces the yield of monomeric IgA obtained with the aid of various purification methods. Aggregates, for example IgG aggregates, also cause among others an increase in anti-complement activity and lead therewith to intolerability reactions after intravenous administration. For this reason, some purification methods according to the state of the art in which a step for the inactivation of viruses is carried out, in paticular a heat treatment step in the presence of stabilizers. Such a method is described in EP 177 836 for example. However, a disadvantage of using stabilizers is that this requires a further removal step. A further disadvantage of using stabilizers is also the simultaneous stabilization of viral proteins and, therewith, the kinetics for inactivation of viruses becomes worse.

Object of the present invention is to separate the immunoglobulins IgG and IgA in an immunoglobulin-containing starting material from each other and also from their high molecular aggregates as well as from other high molecular contaminating substances which were either already present in the starting material or were formed during the purification steps by a method which is simple to carry out and easily transferred to large scale production.

The above object is solved according to the invention by a method which is characterized in that (i) IgG and optionally IgA are adsorbed to a solid inorganic carrier material, (ii) IgA, optionally after selective desorption, is isolated from the eluate whereas IgG remains on the carrier material, and optionally (iii) IgG is isolated from the adsorbate.

The term "eluate" is understood according to the invention as an aqueous solution which is obtained by treatment of the starting material with the carrier material according to the invention, independent of whether an adsorption of IgA to the carrier material and subsequently desorption of the same occurs or whether IgA is not adsorbed to the carrier material at all and remains in solution. The term "adsorbate" from which IgG is optionally isolated according to the invention means that IgG is adsorbed to solid carrier material. IgG can be isolated from the adsorbate by desorption of IgG from the carrier material.

According to the invention, plasma, serum or a suitable plasma fraction is used as immunoglobulin-containing starting material. Furthermore, the starting material can also be secretions, for example mucous secretions. Preferably, a starting material of human origin is used. In a particularly preferred embodiment, plasma and/or plasma fractions are used which are optionally first treated according to the method of Cohn with ethanol and the Cohn II+III-fraction is then employed as starting material for the method according to the invention.

Preferably, poorly soluble salts are considered as an inorganic carrier material, for example compounds from the elements of the second to fourth main group, such as magnesium silicates, aluminium oxides or silicates in the form of silicic acid or diatomaceous earth. The inorganic carrier material for the separation of IgA and IgG according to the invention is preferably a poorly soluble alkaline earth salt such as calcium phosphate and most preferably hydroxylapatite, especially ceramic hydroxylapatite.

The conditions for the adsorption to the inorganic carrier material can be selected such that IgG and optionally IgA are adsorbed. Preferably, high molecular proteins and/or protein aggregates are also adsorbed to the carrier material. The high molecular substances can be considered as those which are already originally present in the starting material or aggregates which are formed during the purification process. Protein aggregates of this type can also represent immunoglobulin aggregates, such as IgG or IgA aggregates for example. In general, immunoglobulins exhibit a strong tendency to aggregate when treated with chemical substances or also when using increased temperatures, etc. This is particularly the case when a heat treatment step for the inactivation of viruses or plasma fractionation steps are carried out. However, the presence of aggregated immunoglobulins is especially problematic in the production of pharmaceutical preparations for intravenous use.

If a buffer with low ionic strength, which is preferably adjusted by phosphate ions, is used in the adsorption, IgG as well as IgA bind to the inorganic carrier material. By slightly increasing the ionic strength of the buffer, a selective adsorption of IgG as compared to IgA can be surprisingly obtained. Thereby, IgA is not or to a low extent adsorped to the carrier material and is therefore not or to a substantially lower extent exposed to physical stress than is the case if adsorption occurs. In this manner, the formation of high molecular IgA aggregates is avoided according to the invention and/or the tendency to form aggregates is reduced.

For example, if a buffer with a pH between 6.5 and 7.5 and an ionic strength corresponding to a concentration of phosphate between 0 to 10 mM is used, IgA quantitatively binds to the solid carrier material. A selective desorption of the IgA occurs by using a buffer whose ionic strength correspondingly lies at a concentration of phosphate between 11 and 100 mM, preferably between 20 and 40 mM, whereas IgG remains on the carrier material. The latter mentioned buffer can then be used for a selective adsorption of the IgG, whereas IgA remains in the eluate.

The buffer for carrying out the method according to the invention preferably does not contain higher organic acids; thus, the buffer does not contain caprylic acid for example which possibly precipitate proteins.

Further purification steps can be performed before or after the method according to the invention. For this, all common methods, such as chromatographic methods, precipitations and/or further adsorption steps for example, are considered. The chromatographic method can be an ion-exchange, affinity, thiophilic and/or a gel permeation chromatography. The precipitations can occur with $ZnSO_4$, rivanol, ethanol, polyethyleneglycol and/or ammonium sulphate for example and can also be carried out as fractionated precipitations. Aside from further inorganic materials, organic materials such as agarose, Sepharose or PEG derivatives are also considered as adsorption materials. Further purification steps can comprise diverse filtration and centrifugation steps.

Preferably, ion-exchange chromatography is carried out as an additional purification method. Most preferably, an additional precipitation step with ammonium sulphate is carried out for example. Optionally, adsorption to protein-G Sepharose is carried out as a further step for selective adsorption of IgG.

All purification steps using a carrier material can be carried out as a batch-method or in a column. The batch-method is to be preferred for a large scale preparation because, in general, larger amounts of starting material can be purified and/or separated in a shorter time therewith.

According to a preferred embodiment, a step for the inactivation of viruses is also carried out. This step can occur anywhere in the purification method according to the invention and/or the further various purification steps. Preferably, a step for the inactivation of viruses is carried out after the treatment with a solid inorganic carrier material.

Any methods known in the art for virus inactivation can be used. Thereby, it is known that a heat treatment is preferably conducted because this also results in the inactivation of non-lipid coated viruses (hepatitis A).

The preparation can be used in dissolved or solid form for carrying out a heat treatment step. If the heat treatment is carried out in solid form, the product which is subjected to the heat treatment preferably has a moisture content of 5 to 70% by weight. According to another preferred embodiment as solid form a lyophilisate is used. The virus inactivation preferably occurs at a temperature in the range between 40 and 80° C., especially in the range between 50 and 65° C. Thereby, the heat treatment is carried out for at least a sufficiently long time for the inactivation of viruses, preferably during a period of 30 minutes to 10 h. Preferably, the heat treatment occurs as a steam treatment, especially according to a method described in EP 159 311. In the mentioned method, which works without the addition of stabilizers, hydroxyl group-containing compounds such as methanol, ethanol or mannite for example can be used instead of water.

It is also possible to carry out the virus inactivation in the presence of stabilizers. Such a method is described in EP 177 833. In this method, the stabilizer protects the relatively labile immunoglobulins against denaturation and maintains their biological activity.

However, aside from a heat treatment, all other methods for inactivation of viruses can also be used. Thus, a solvent/detergent treatment according to EP 131 740 or detergent treatment according to EP 50 061 can be applied for example. Methods which include UV-irradiation together with β-propiolactone as methods for inactivation of viruses are also suitable.

Chemical or physical treatments in the presence of a polyether as described in DE 44 34 538 are suitable as further treatments for subjecting immunoglobulin-containing fractions to a method for inactivation of infectious agent. For this purpose, polyhydroxy ethers such as polyalkylene glycol for example and especially polyethylene or polypropylene glycol are considered as polyethers.

The use of neutral peptide hydrolases such as trypsin or chymotrypsin for example according to EP 247 998 is also to be mentioned as a further possibility for the inactivation of pathogenic agents which are capable of replication.

It can also be suitable to combine the heat treatment with one or more other known and common methods for virus inactivation, especially with a UV-irradiation, a treatment with tensides and/or a treatment with a solvent/detergent system. The individual process steps can occur simultaneously (for example heat treatment with simultaneous UV-irradiation) or in any other order.

The different mechanisms of action of these inactivating methods can be utilized by a combination of the heat treatment with one or more other methods for virus inactivation, whereby the virus safety of the product can be increased further.

A proven measure for depletion of viruses is also the nanofiltration of a solution containing the immunoglobulins.

Optionally, IgG is also isolated from the adsorbate, whereby the IgG is provided after desorption from the solid inorganic carrier material. However, the IgG can also be purified by further methods as already described for the isolation of immunoglobulins above. The further purification methods for IgG correspond to techniques known in the state of the art (for example see AT 0383 737, Immuno AG, or J. J. Langone in J. Immunol Methods 55 (1982), P. 277–296).

With the method according to the invention IgA can be mereley recovered, but additionally also IgG preparations can be obtained.

Suitably, dialysis against water can also be carried out before the heat treatment, whereby impurities which are optionally still present, especially optionally added or present stabilizing substances, can be considerably removed.

The invention also comprises an IgA preparation which is obtained according to the method of the invention. This IgA preparation differs from preparations known in the art in its properties.

Thus, an IgA preparation is obtained according to the invention which is essentially free of IgG. According to the invention the term "IgA essentially free from IgG" means an IgA which comprises less than 15% IgG, preferably 10% and most preferably 2 to 5% IgG with respect to total immunoglobulin.

The purity of the IgA preparation according to the invention lies above 70% and preferably amounts to 80 and/or 85%, whereby a IgA preparation according to the invention of 90 to 92% purity with respect to total protein is most preferred.

As already mentioned above, the conditions for the adsorption to the inorganic carrier material can be selected in such a manner that IgG is adsorbed, whereas IgA is not adsorbed, and is recovered from the aqueous solution and/or suspension referred to as the eluate. According to this method variation, IgA is not exposed to any physical stress during this purification step. Thereby, alterations in the molecule, for example conformation alterations as they can occur as a result of the adsorption, are mainly avoided. According to the invention, it is preferred to also select the conditions in further purification steps such that an adsorption of IgA is avoided. This is of importance because physical stress triggers a tendency towards aggregation formation of proteins in general and in particular of immunoglobulins.

According to the method of the invention, a stable IgA solution is obtainable which is distinguished by a low tendency towards aggregate formation and is suitable for pharmaceutical use. Preferably, the IgA is not adsorbed to an inorganic carrier, and most preferably, the IgA is not adsorbed to any carrier material during further purification steps.

This IgA preparation is stable enough such that it can be subjected to a heat treatment or lyophilization without considerable aggregate formation.

Preferably, the IgA is not adsorbed to an inorganic carrier material, and most preferably, the IgA is also not adsorbed to any carrier material during further purification steps.

As already mentioned, the IgA solution according to the invention is distinguished by a low tendency to form aggregates. This tendency to form aggregates can be determined for example by means of an easily performed test: The preparation to be examined is incubated in a physiological medium as a solution, optionally after reconstitution of the lyophilisate, at a concentration of 2 mg IgA/ml or 0.5 mg IgA/ml at a temperature of 63° C. for 20 minutes and then the amount of aggregates formed is determined by means of a well-known method, for example by means of electrophoretic methods or by means of a gel filtration analysis. The solution according to the invention then has an aggregate content of less than 50%, preferably less than 40%, more preferably less than 30%, further preferred less than 20%, still more preferred less than 10% and most preferred less than 5%.

The test can also be carried out at other temperatures, preferably of at least 60° C. under the same conditions as already described in doing so, the time for incubating the sample to be examined is then to be correspondingly shortened or extended by 4 min per ° C. For example, the test can be carried at a temperature of 60° C. for 32 min or by 65° C. for 12 min.

The IgA solution prepared according to the method of the invention is distinguished by the native confirmation of the IgA. This is particularly important for biological functions for which an intact immunoglobulin is a pre-requisite as this can be determined by tests for determination of toxin neutralization, down-modulation of cytokines and/or inhibition of the formation of oxygen radicals for example.

Aggregates are understood as molecule associations which have a molecular weight of more than 400 kD. Generally, high molecular aggregates have a molecular weight of more than 600 kD. According to definition, IgA monomers have a molecular weight in the range between 150 and 180 kD. The molecular weight of the IgA dimers lies in a range between 300 and 360 kD. Under certain circumstances, the IgA dimer can also contain the J-chain and/or the secretory component.

According to the method of the invention, a stable IgA solution is obtainable which has less than 10% aggregates for example, preferably the aggregate portion lies under 8% and most preferably the solution has aggregate portion of less than 5%.

The content of dimers in the solution according to the invention amounts up to 10% for example, preferably up to 8%, most preferably the solution contains 1 to 2% dimers.

The content on IgA monomers can lie between 80 and 99%, preferably the portion of monomeric IgA lies around 90%.

The IgA solution according to the invention is suitable for pharmaceutical application and is stable in storage. Thus, the IgA solution according to the invention is stable when stored at 4° C. up to 4 years, preferably up to 2 years, or at room temperature for 1 month up to 2 years, without substantial aggregate formation, i.e. less than 10% aggregate content in the solution.

At higher temperatures, as they are applied in the corresponding method for virus inactivation which are optionally present in the solution for example, i.e. at temperatures between 50 and 80° C. for example, preferably between 60 and 65° C., the solution according to the invention is also stable and has a low tendency to form aggregates. This reduced tendency to form aggregates can be established by means of the test systems described above.

The sub-classes IgA1 and IgA2 are preferably present in a ratio in the IgA solution according to the invention which corresponds to the composition of native IgA. Preferably, this concerns polyvalent IgA.

The IgA preparation according to the invention can be combined together with a common pharmaceutical carrier and/or solution agents. It can be present in liquid or lyophilized form and is stable in storage.

Pharmaceutical compositions which contain the IgA according to the invention can also comprise other active ingredients (active substances) as long as these are compatible with IgA and are suitable and useful for the determined purpose of the pharmaceutical composition.

The production of the pharmaceutical composition occurs according to known methods and is especially oriented in accordance with the type of the intended administration form. The administration of the IgA preparations isolated according to the invention can occur in a local, mucosal, for example oral, or systemic manner.

Pharmaceutical compositions containing the IgA preparation isolated according to the invention are especially suitable for the prevention and treatment of inflammations, infections and/or allergies. The dosage depends on the mode of administration and the frequency of administration as well as the degree and severity of the disease. When high total doses of IgA are to be administered, it is frequently preferred to administer IgA in several small dosage amounts distributed throughout the day. For example, IgA can be administered orally (normal 1 to 10 g/day or in severe cases more) preferably in 3 or more doses. However, the dosage is also especially orientated in accordance with the general physical condition and age of the patients and according to the severity of the disease.

The administration of IgA in a systemic manner is particularly preferred, for example by means of intravenous injections, continuous infusions or both. Typically, 50 to 2000 mg IgA/kg/day are administered. In rare cases, administration can also occur intramuscularly, normally with a dosage of 50 to 100 mg IgA/kg/day.

Additionally, the IgA isolated according to the invention can also be administered mucosally, for example by means of inhalations (up to 10 ml/day, 10 to 100 mg IgA/ml), nasally (15 to 200 mg/ml) with the aid of sprays or drops or locally by intra-articular injections (which according to need contain 1 to 5 ml of a solution of 10 to 100 mg IgA/ml). Other modes of administration comprise suppositories (100 to 1000 mg IgA/dose) and transdermal plasters. Transdermal plasters are particularly suitable to treat skin inflammations.

Those forms of administration are especially considered which are common for the prevention and treatment of viral infections, especially oral forms of administration such as capsules, tablets, granulates, pellets, mini-pellets and microcapsules for example. In the treatment of viral intestinal infections, it is preferred to provide the granulates and/or mini-pellets, etc. with a customary gastric juice-resistant, intestine-soluble coating for this.

Figure 2:
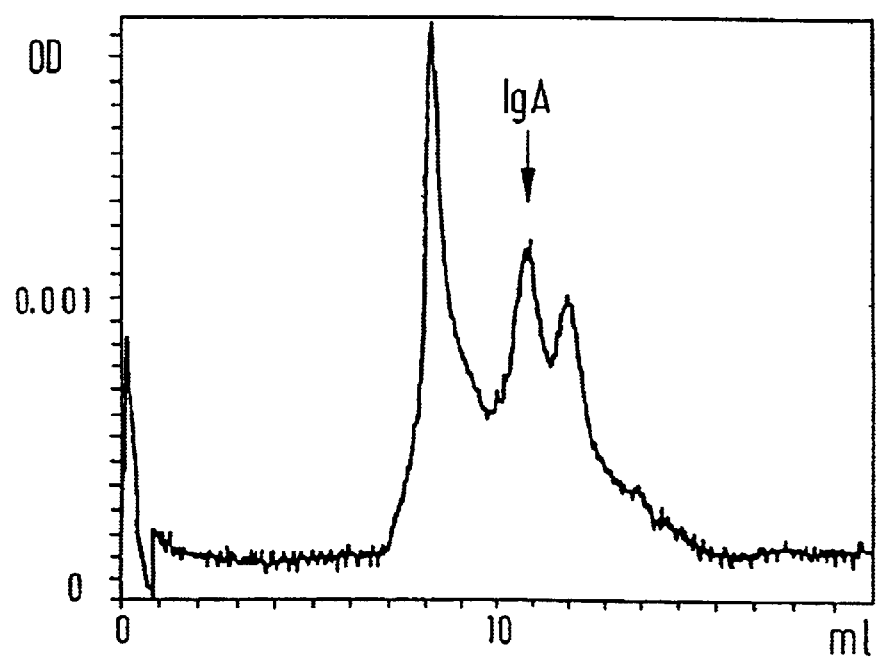
Figure 3:
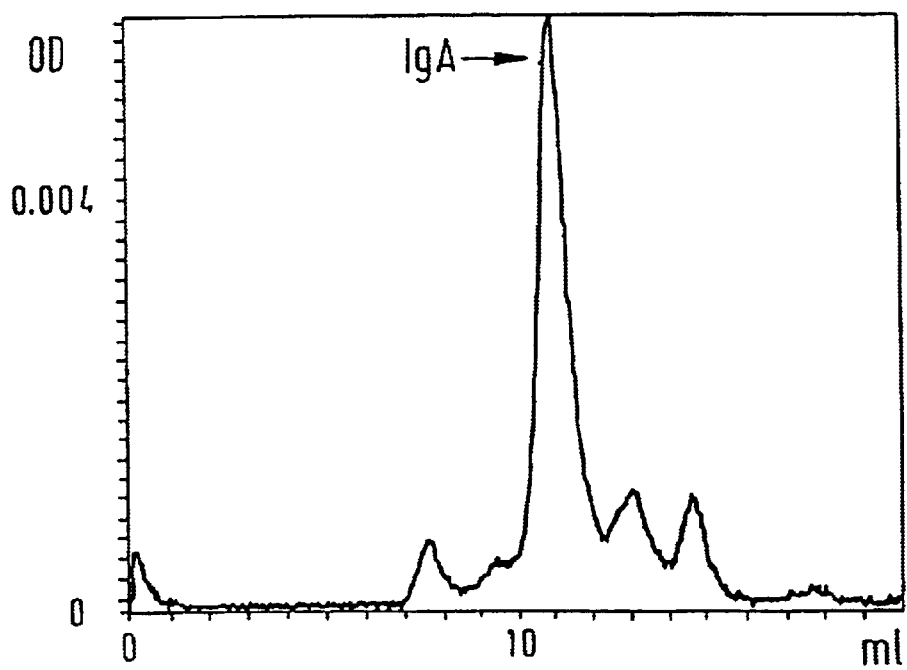
Figure 4:
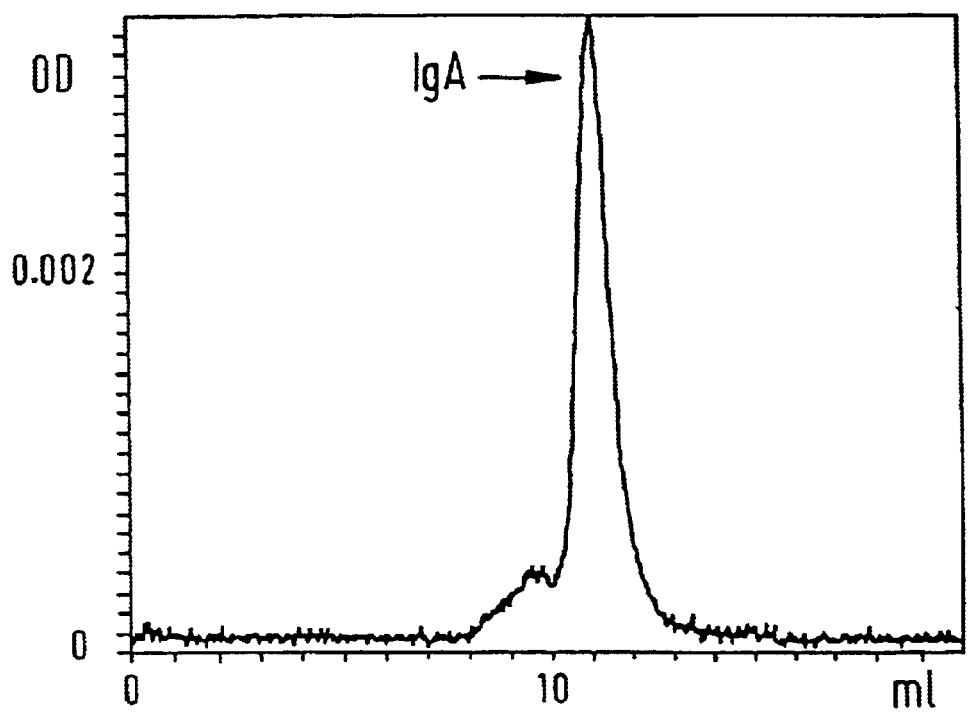

The elution diagrams shown in the accompanying figures were obtained by gel filtration analysis of the intermediate steps and/or final step respectively. The figures represent the following:

FIG. 1. Gel filtration analysis of the starting material;

FIG. 2. Gel filtration analysis of the material obtained after Fractogel TMAE according to example 1;

FIG. 3. Gel filtration analysis of the material obtained after hydroxylapatite treatment according to example 1;

FIG. 4. Gel filtration analysis of the material obtained after ammonium sulfate precipitation according to example 1.

The arrow indicates the respective IgA-containing peak.

The following examples are meant to more closely illustrate the invention without limiting the invention to them.

EXAMPLE 1

As described in EP 506 651, a Cohn II+III-fraction was produced from human plasma which was extracted with a phosphate-acetate buffer. Ethanol was added at the pH value of 5.3 and a temperature of −2° C. up to a concentration of 12%, whereby a precipitate was formed which was separated. The obtained paste was extracted and the extract was treated with lysine-agarose to separate plasminogen. The non-bound material was further treated according to the invention:

The lysine-agarose supernatant was centrifuged 60 min at 18900×g at 4° C. in order to separate the insoluble components. The precipitate was discarded. The supernatant was dialysed at room temperature on an Amicon Spiral Module S1Y30 Cross Flow against the three-fold sample volume of 50 mM sodium acetate/acetic acid buffer, pH 5.0, and subsequently centrifuged for 15 min at 18900×g at 4° C.

The dialysed material was mixed with an anion exchanger in a batch method. For this, the sample was mixed with an equal volume of ion exchanger (Fractogel EMD TMAE 650 (M) particle size 0.04 to 0.09 mm; Merck, Darmstadt, DE; suspended 1:2 in 50 mM sodium acetate/acetic acid buffer, pH 5.0) such that 2 ml gel suspension was present per 20 mg protein. The suspension was stirred overnight at 4° C. Non-bound material was separated over a suction filter and the gel was washed twice with 50 mM sodium acetate/acetic acid buffer, pH 5.0. Subsequently, the gel was stirred 2 h at 4° C. with 50 mM sodium acetate/acetic acid buffer+0.5 M NaCl, pH 5.5. Then, the gel was separated over a suction filter from the proteins eluted with this buffer. The elution was carried out twice.

The eluted material was dialysed against buffer A (PBS, pH 7.4). 3% of buffer B (0.5 M $NaH_2PO_4/Na_2HPO_4$+150 mM NaCl, pH 6.8) was added to the retained material. This material was mixed with hydroxylapatite (BioRad, Richmond, Calif./USA; Macro Prep ceramic hydroxylapatite; 20 micron) in a batch method. For this, hydroxylapatite was equilibrated in a mixture of 97% buffer A (PBS, pH 7.4) and 3% buffer B (0.5 M $NaH_2PO_4/Na_2HPO_4$+150 mM NaCl, pH 6.8) and suspended in the same buffer mixture. 1 ml hydroxylapatite was added per 2 mg IgA. The batch was stirred overnight at 4° C. The supernatant was suction filtered and the hydroxylapatite was washed at 4° C. with a mixture of 97% buffer A (PBS, pH 7.4) and 3% buffer B (0.5 M $NaH_2PO_4/Na_2HPO_4$+150 mM NaCl, pH 6.8). The wash supernatant was suction-filtered and combined with the first supernatant.

The eluates of the hydroxylapatite batch method were mixed, immediately or after concentration, by stirring with ammonium sulfate which was added to a concentration of 1.8 M. Additionally, the material was stirred 1 h at room temperature and subsequently the precipitate which was formed was centrifuged 15 min at 2410×g. The precipitate was resuspended in PBS, pH 7.4, and dialysed against distilled water (dialysis tube from Spectra/Por, Nr. 2, MWCO 12–14.000). The precipitate formed during the dialysis was centrifuged and the supernatant was sterile filtered.

The product produced in this manner was analysed:

The analysis over gel filtration was carried on an analytical Superdex 200 HR 10/30 FPLC column (Pharmacia-LKB) with PBS as a running buffer and a flow rate of 0.5 ml/min on a FPLC apparatus (Pharmacia-LKB). The optical density (OD) was measured at 280 nm in a flow-through cell and recorded against the elution volume (ml).

IgA and IgG were determined by means of radial immunodiffusion (Mancini, G. et al, Immunochemistry 2 (1965) 253–254) and the total protein content was determined according lo the method of Lowry, O. H. et al. (J. Biol. Chem. 193 (1951) 265–275).

Although it was shown that the ion exchange treatment brought about a partial enrichment of IgA (see Table 1), a portion of IgA, high molecular proteins and/or aggregates was still present (see FIGS. 1 and 2).

The hydroxylapatite treatment clearly increased the ratio of IgA to IgG (see Table 1 and FIG. 3). This means that IgA and IgG were separated by this treatment.

The end product consisted mostly of IgA monomers as well as a small portion of IgA dimers which were formed in solution from IgA monomers (see Table 1 and FIG. 4).

TABLE 1

| Treatment | Total protein mg | IgA mg | IgG portion mg | Ratio of IgA/protein in % | Ratio of IgA:IgG |
|---|---|---|---|---|---|
| Starting material | 5745 | 1084 | 770 | 19 | 1.4:1 |
| Fractogel | 1987 | 591 | 110 | 30 | 5.4:1 |

TABLE 1-continued

| Treatment | Total protein mg | IgA mg | IgG portion mg | Ratio of IgA/protein in % | Ratio of IgA:IgG |
|---|---|---|---|---|---|
| Hydroxyl apatite | 305 | 199 | 14 | 65 | 14.2:1 |
| Ammonium sulfate | 132 | 120 | 5 | 91 | 24.0:1 |

What is claimed is:

1. A method for isolating IgA from an immunoglobulin-containing starting material, comprising
   (i) contacting the immunoglobulin-containing starting material with a solid inorganic carrier material such that IgG from the immunoglobulin-containing starting material is adsorbed to the solid inorganic carrier material and an eluant and adsorbate are formed;
   (ii) isolating IgA from the eluant, wherein IgG remains on the solid inorganic carrier material, and wherein the isolated IgA has a low tendency to form aggregates, and
   (iii) isolating IgG from the adsorbate.

2. The method according to claim 1, wherein the solid inorganic carrier material is hydroxylapatite.

3. The method according to claim 1, further comprising subjecting the isolated IgA to a viral inactivation treatment.

4. A method of isolating IgA from an immunoglobulin-containing starting material, comprising
   (i) contacting the immunoglobulin-containing starting material with a solid inorganic carrier material selected from the group consisting of magnesium silicates, silicic acid, diatomaceous earth and calcium phosphate, wherein during the contacting IgG from the immunoglobulin-containing starting material is adsorbed to the solid inorganic carrier material and an eluant is formed, and
   (ii) isolating IgA from the eluant, whereas IgG remains on the solid inorganic carrier material, and wherein the isolated IgA has a low tendency to form aggregates.

5. The method according to claim 4, further comprising subjecting the isolated IgA to a viral inactivation treatment.

6. The method according to claim 4, wherein the solid inorganic carrier material is hydroxylapatite.

7. A method of isolating IgA that has a low tendency to form aggregates, comprising
   (i) contacting an immunoglobulin-containing starting material with a solid inorganic carrier material selected from the group consisting of magnesium silicates, silicic acid, diatomaceous earth and calcium phosphate, such that IgG from the immunoglobulin-containing starting material is adsorbed to the solid inorganic carrier material and an eluant is formed, wherein IgA is not bound to the solid inorganic carrier material, and
   (ii) isolating IgA from the eluant.

8. The method according to claim 7, wherein the solid inorganic carrier material is hydroxylapatite.

9. The method according to claim 7, further comprising subjecting the isolated IgA to a viral inactivation treatment, wherein the virally-inactivated IgA has a low tendency to form aggregates and is suitable for use in a pharmaceutical solution.

10. The method according to claim 7, further comprising subjecting the isolated IgA to a viral inactivation treatment.

* * * * *